(12) United States Patent
Bolger et al.

(10) Patent No.: US 6,770,096 B2
(45) Date of Patent: Aug. 3, 2004

(54) INTERBODY SPINAL STABILIZATION CAGE AND SPINAL STABILIZATION METHOD

(75) Inventors: Ciaran Bolger, Bristol (GB); John Bolger, Dublin (IE)

(73) Assignee: Spinevision S.A. (FR)

( * ) Notice: Subject to any disclaimer, the term of this patent is extended or adjusted under 35 U.S.C. 154(b) by 261 days.

(21) Appl. No.: 10/109,254

(22) Filed: Mar. 27, 2002

(65) Prior Publication Data

US 2003/0187436 A1 Oct. 2, 2003

Related U.S. Application Data

(63) Continuation-in-part of application No. 10/019,712, filed as application No. PCT/FR00/01892 on Jul. 3, 2000.

(30) Foreign Application Priority Data

Jul. 1, 1999 (FR) .............................................. 99 08501

(51) Int. Cl.[7] ................................................. A61F 2/44
(52) U.S. Cl. .................................................... 623/17.16
(58) Field of Search ....................... 606/61; 623/17.11, 623/17.13, 17.15, 17.16

(56) References Cited

U.S. PATENT DOCUMENTS

| 5,123,926 A | * | 6/1992 | Pisharodi | 623/17.13 |
|---|---|---|---|---|
| 5,522,899 A | * | 6/1996 | Michelson | 606/61 |
| 5,658,335 A | * | 8/1997 | Allen | 623/17.16 |
| 5,683,394 A | | 11/1997 | Rinner | |
| 5,702,391 A | * | 12/1997 | Lin | 606/61 |
| 5,800,547 A | * | 9/1998 | Schafer et al. | 623/17.16 |
| 5,800,550 A | * | 9/1998 | Sertich | 623/17.16 |
| 6,179,873 B1 | * | 1/2001 | Zientek | 623/17.11 |
| 6,302,914 B1 | * | 10/2001 | Michelson | 623/17.16 |
| 6,371,987 B1 | * | 4/2002 | Weiland et al. | 623/17.11 |
| 6,527,803 B1 | * | 3/2003 | Crozet et al. | 623/17.11 |

FOREIGN PATENT DOCUMENTS

| DE | 43 27 054 | 4/1995 |
|---|---|---|
| EP | 0 951 879 | 10/1999 |
| WO | WO 97/06753 | 2/1997 |
| WO | WO 97/46165 | 12/1997 |
| WO | WO 97/48352 | 12/1997 |
| WO | WO 99/42062 | 8/1999 |
| WO | WO 99/66867 | 12/1999 |

* cited by examiner

*Primary Examiner*—Eduardo C. Robert
(74) *Attorney, Agent, or Firm*—Bachman & LaPointe, P.C.

(57) ABSTRACT

The present invention relates to an interbody spinal stabilization method and an interbody spinal stabilization cage. The cage has a parallelepipedic shape and comprises a central hollow space intended to be filled with bone fragments. The cage also comprises anchoring device(s) having an overall S shape and opening onto lateral faces connecting with adjacent vertebrae, actuated by at least one actuation device opening into a front face. The anchoring device(s) each have at least one main cutting edge.

23 Claims, 7 Drawing Sheets

INTERBODY SPINAL STABILIZATION CAGE AND SPINAL STABILIZATION METHOD

CROSS-REFERENCE TO RELATED APPLICATION(S)

This application is a continuation-in-part of U.S. Ser. No. 10/019,712, filed Dec. 28, 2001, entitled INTERBODY SPINAL STABILIZATION CAGE, now abandoned, which claims priority to PCT Application PCT/FR00/01892 filed on Jul. 03, 2000.

BACKGROUND OF THE INVENTION

The present invention relates to the field of spinal orthopaedics, and more particularly to that of interbody cages.

Such prostheses are intended to stabilize pathological spinal segments and induce bone consolidation by means of the fusion of the two segments. These cages are generally made from titanium, carbon or biocompatible composite material and receive bone grafts.

For example, it is possible to refer to the French patent application FR 2764795 disclosing an interbody cage according to the prior art. This cage comprises a central hollow space intended to be filled with bone fragments. It comprises, on its transverse section, two wide, convex faces, each equipped with a central opening, two narrow faces each equipped with a central opening, said narrow faces comprising slanting toothing distributed at either end of the central opening of the narrow faces. It also comprises a convex closed front end and a rear end comprising at its centre a polygonal housing to receive an adjustment device. A fitting key equipped with a polygonal fitting and a threaded rod cooperates with the cage according to the invention to insert it by means of impaction between the vertebrae and stabilize it by means of rotation after impaction.

Another French patent application published under the number FR2761879 discloses an implant which comprises, on its two diametrically opposite sides intended to come into contact with the spongy bone of the vertebrae after implantation, a plurality of separate openings, offset at an angle with reference to the others by an interval corresponding roughly to half the length of an opening, such that one of these openings is located opposite the part of the wall of the implant which separates two longitudinally adjacent openings.

Another patent application FR2717068 discloses an interbody cage to be inserted frontally between two vertebrae comprising two roughly parallel branches to come into contact with the vertebral bodies, a bridge connecting the rear ends of the branches after insertion of the cage between the two vertebrae. The cage enables preoperative setting of the lordosis angle between the two vertebrae. A cage holder is connected in a detachable manner to the cage to insert the cage between the two vertebrae. After the removal of the cage holder, a screwdriver turns a screw wherein the rear end is attached to the distance piece and screwed into one of the branches to separate the two cage branches.

It was also proposed in the U.S. Pat. No. 5,800,550 to produce an interbody cage comprising toothed cylinders which can be pushed vertically into the vertebrae, by means of a tool equipped with a screw thread, in order to hold the interbody cage in place.

It was also proposed in the German patent application No. DE 4327054 to produce an interbody cage comprising a camshaft used to raise support eyebolts.

It was also proposed in the international patent application No. WO 97/06753 to produce an interbody cage comprising a more or less cylindrical hollow body 1, 51 equipped with one or more openings 9, 10, 59, 59', 60, 60'. The hollow body 1, 51 may be broadened in an adjustable manner by adjustment components 18, 19, 65, 66 and comprises fixation components 24, 25, 69, 70, 71, 72 used to fix it on vertebrae.

It was also proposed in the international patent application No. WO 97/46165 to produce an interbody cage comprising at least two basic screws 1, two locking parts 2 preventing the rotation of the vertebra and a connection part 3, 4, 5.

The problem posed with these interbody cages according to the prior art is that of provisional fixation before bone fusion has taken place. Indeed, it is vital for the cage to remain in position. The solutions according to the prior art are not satisfactory since they require direct or indirect impacting of the cage in the intervertebral space.

The major drawbacks of the devices according to the prior art lie both in the fact that they do not allow perfect stabilization of the interbody cage in the spinal segments, particularly during extension and/or rotation movements of the spinal column and in the fact that they do not really allow the ablation of the interbody cage.

SUMMARY OF THE INVENTION

The purpose of the present invention to propose an enhanced interbody cage allowing implantation by the cervical, thoracic or lumbar route, by means of a frontal or rear surgical procedure, guaranteeing effective fixation of the cage before bone fusion and once bone fusion has taken place, and allowing the removal of the cage after bone fusion.

The purpose of the cage according to the invention is to make it possible to keep the intervertebral space constant in order to prevent the distraction of the vertebral bodies.

For this purpose, the broadest embodiment of the invention relates to an interbody spinal stabilization cage according to claim 1.

An anchoring point is, by definition, composed of a lock comprising no degree of freedom. The interbody cage anchored in this way by anchoring means locks the vertebrae in terms of compression, extension and rotation, in order to form a perfectly attached assembly.

Preferentially, the actuation means comprise a rotation actuation head and are mobile in rotation in both directions, to allow reversibility of the anchoring means.

According to a preferred embodiment, said anchoring means have an overall S shape and the centre of gravity of the S shape coincides with the axis of the actuation means.

Advantageously, each anchoring means comprise at least one radial cutting edge roughly perpendicular to the axis of the actuation means, to allow good penetration of the anchoring means in the bone substance when the cage is fitted and possibly during its ablation.

Advantageously, each anchoring means also comprise at least one return cutting edge roughly parallel to the main cutting edge to allow good penetration of the anchoring means in the bone substance during the ablation of the cage.

Also advantageously, each anchoring means comprise a slot, to allow bone regrowth between the arms of the anchoring means. The co-operation obtained in this way between the anchoring means and the bone regrowth guarantees perfect support of the vertebrae in terms of compression, extension and rotation.

In addition, the edges of these slots are preferentially at least partially cutting, to allow the production of a slit for the release of the anchoring means and the ablation of the interbody cage.

Also advantageously, the cage according to the invention comprises force locking/unlocking means of the anchoring means in their anchored position.

Finally, advantageously, said actuation means comprise in their centres a hole wherein the walls are threaded, to be able to position one or more additional components, such as a fixation screw, in the axis of the actuation means.

The present invention also relates to a spinal stabilization method using the interbody spinal stabilization cage according to the invention, positioned between two vertebrae, the actuation means of the interbody cage being used to actuate said S-shaped anchoring means in order to enable them to change from a retracted position wherein they are positioned inside said cage to a projecting position wherein their ends come out of said cage, wherein said cage is inserted between two spinal vertebrae with the S-shaped anchoring means in the retracted position, and wherein the actuation means are actuated so that the ends of the S-shaped anchoring means come out of the cage and penetrate the vertebrae.

Advantageously, the vertebral disks of the vertebrae between which the interbody cage is to be positioned are cut beforehand using a cutting instrument, in order to prevent the distraction of the vertebrae when the anchoring means penetrate.

Also advantageously, said vertebrae are compressed using a correction instrument, during the anchoring of said interbody cage.

Indeed, a significant distraction strain on the vertebrae during the positioning of the anchoring means is not acceptable. Depending on the torque required for the penetration of the anchoring means, a compression/distraction type instrument may be used to keep the vertebrae in place, and compress them, trapping the cage between the vertebrae for the positioning of said anchoring means.

The instrument can thus be used:
- in the vertebral distraction position to work on the vertebral disks before positioning the cage,
- in the vertebral compression position to be able to lock the vertebrae temporarily and compress the cage between the vertebrae, to position the anchoring means, and favour, at least partly, the retention of compression of the cage between the vertebrae after the ablation of the instrument. This compression is obtained by means of the advantageous form of the anchoring means.

BRIEF DESCRIPTION OF THE DRAWINGS

The invention will be understood more clearly upon reading the following description, with reference to the non-restrictive example illustrated in the appended figures where.

DETAILED DESCRIPTION OF THE PREFERRED EMBODIMENTS

The interbody cage 1 according to the invention has an overall parallelepipedic shape and delimits a hollow inner space 4 opening by means of slots provides on the different faces, particularly on the lateral 5, 5' and front 6 faces. The inner space 4 is intended to be filled with bone fragments taken from the patient. These bone fragments are intended to initiate fusion of the vertebrae between which the interbody cage is placed.

These bone fragments may be replaced by synthetic bone.

The front face 6 comprises a slot used to access the rotation actuation head 7 of the actuation means 2.

In this way, using the actuation means, the anchoring means each have two extreme positions: a retracted position wherein they are positioned inside the cage and an anchored position wherein that have a maximum clearance outside the cage. Between these two extreme positions, the anchoring means comprise a plurality of intermediate anchoring positions.

To anchor the cage, the cage is inserted between two spinal vertebrae 21, 21', the S-shaped anchoring means being in the retracted position, and the actuation means are then actuated so that the ends of the S-shaped anchoring means come out of the cage and penetrate the vertebrae.

Figure 1:
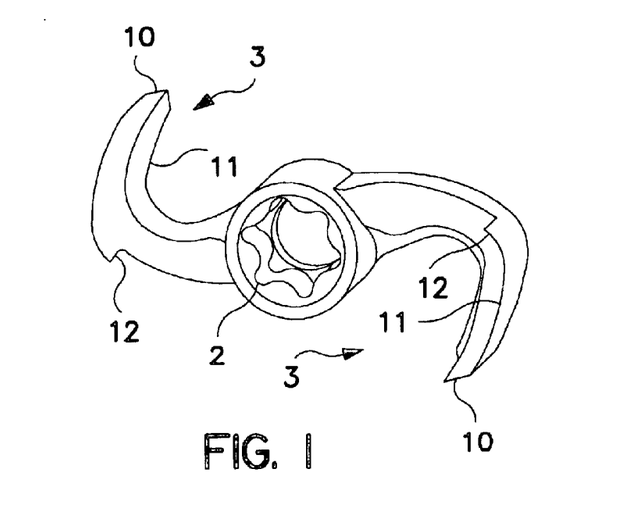
FIGS. 1 and 2 respectively illustrate a perspective view of two pairs of S-shaped anchoring means according to an embodiment of the anchoring means of the interbody cage according to the invention.
Figure 2:
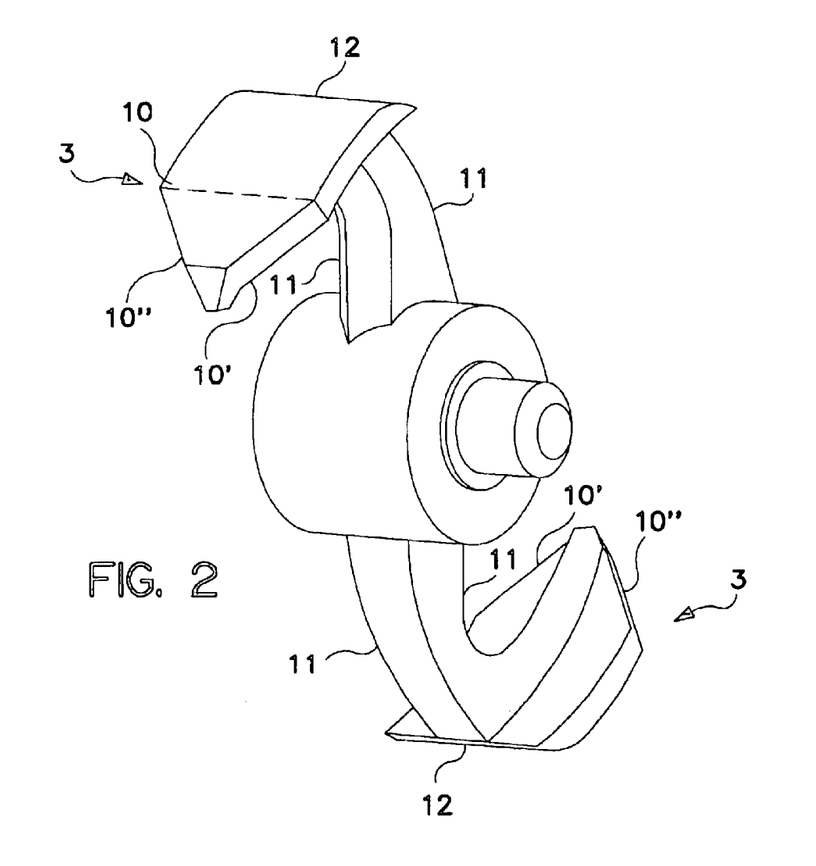
Figure 3:
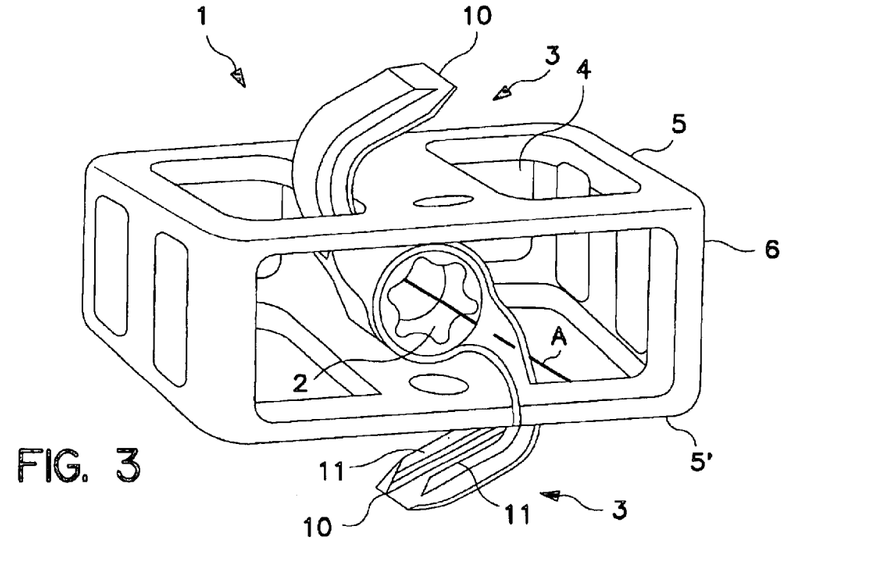
FIG. 3 illustrates a perspective view of an interbody cage according to the invention with anchoring means.

In a preferred embodiment of the invention, said anchoring means 3 have an overall S shape, as illustrated in FIGS. 1 and 2, and the centre of gravity of the S shape is positioned on the axis A of the actuation means 2, as illustrated in FIG. 3.

In this version, each anchoring means 3 preferentially comprise at least one radial cutting edge 11, positioned on a radius of the anchoring means, roughly perpendicular to the axis of the actuation means, on the edge of the connection arms of the anchoring means, and at least one return cutting edge 12 roughly parallel to the main cutting edge 10, as illustrated in FIGS. 1 and 2.

FIG. 2 illustrates a version of the invention wherein said main cutting edge 10 forms the base of an at least isosceles or equilateral triangle, equipped with cutting sides forming sharp edges 10',10".

In this figure, each anchoring means 3 comprise two radial cutting edges 11 positioned roughly on the same radius of the anchoring means 3, on opposite edges, inside and outside, of the connection arms.

In FIG. 3, each anchoring means 3 comprise two radial cutting edges 11 positioned side by side on the inner face of the connection arms.

Figure 4:
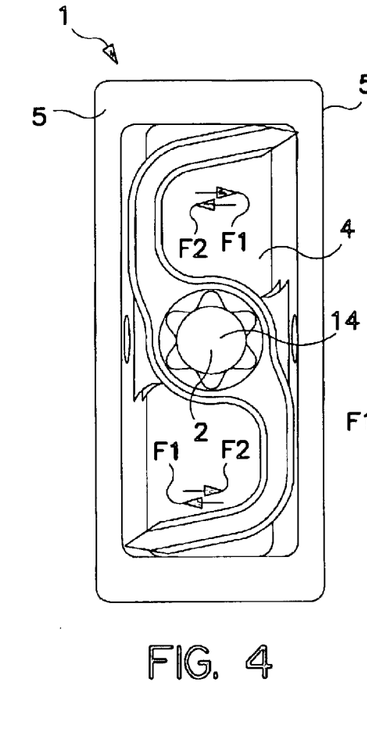
FIGS. 4 and 5 respectively illustrate a front view of the interbody cage in FIG. 3, in the retracted position and in the anchoring position.
Figure 5:
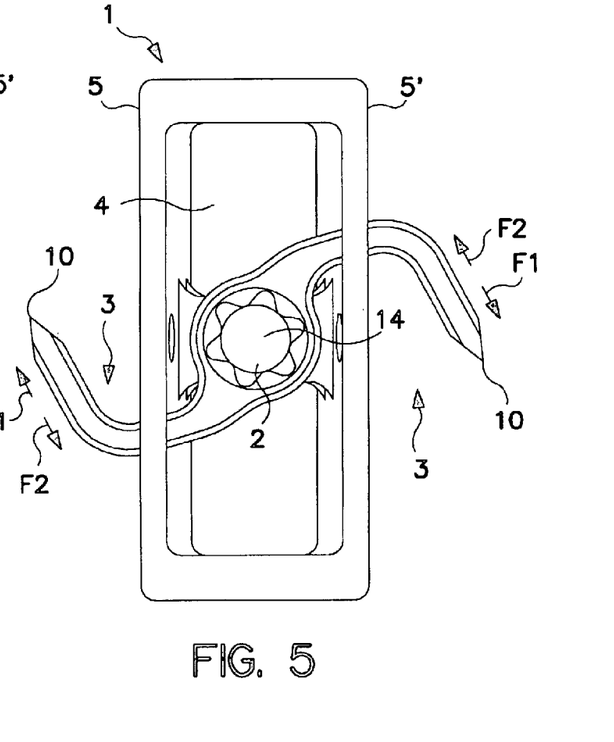

The cutting movement enabling the anchoring of the cage is illustrated by the arrows F1 in FIGS. 4 and 5, while the ablation movement is illustrated by the arrows F2.

Figures 6, 7:
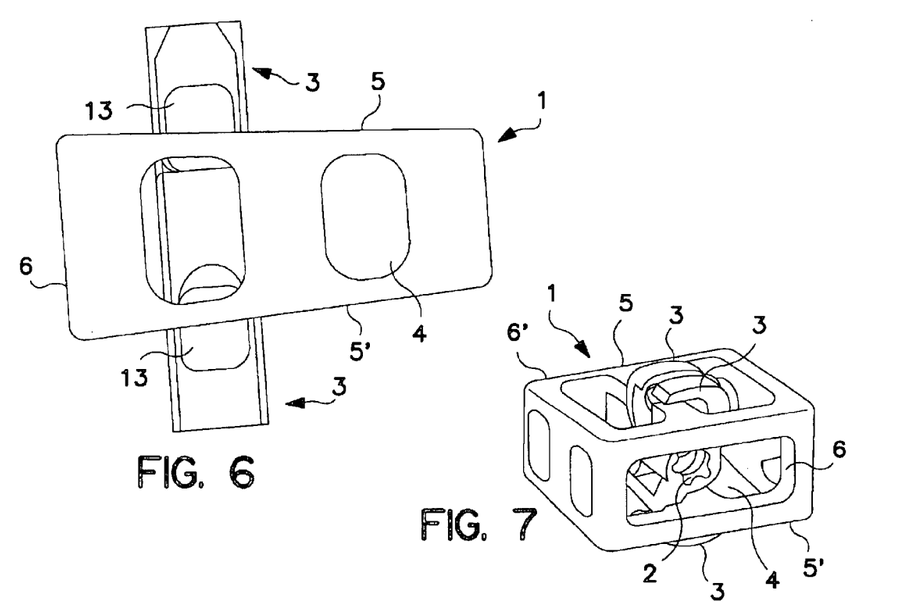
FIG. 6 illustrates a side view of an interbody cage according to the invention with anchoring means.
FIG. 7 illustrates a perspective view of an interbody cage according to the invention with a double pair of anchoring means.

In addition, each anchoring means preferentially 3 comprise a slot 13 wherein the edges are at least partially cutting, as illustrated in FIG. 6.

To be able to lock the anchoring means 3 in the anchoring position, the cage according to the invention preferentially comprises force locking/unlocking means of the anchoring means 3 in their anchored position, composed, for example, of a boss intended to co-operate with a recess.

Preferentially, the interbody cage 1 according to the invention, as illustrated in FIG. 7, comprises two pairs of anchoring means 3 turning, for example, in two opposite directions, each actuation means 2 of each pair of anchoring means 3 opening onto the same front face 6.

Figure 8:
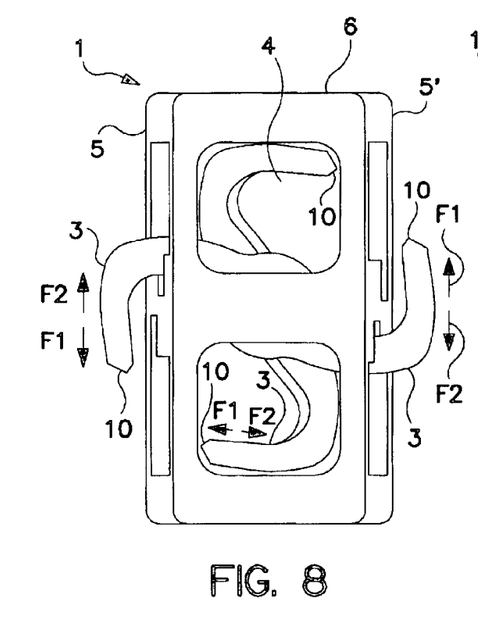
FIGS. 8 and 9 respectively illustrate a front view of the interbody cage in FIG. 7, in the anchoring position and in the anchored position.

In this version, the cutting movement enabling the anchoring of the cage is illustrated by the arrows F1 in FIG. 8, while the ablation movement is illustrated by the arrows F2.

Figure 9:
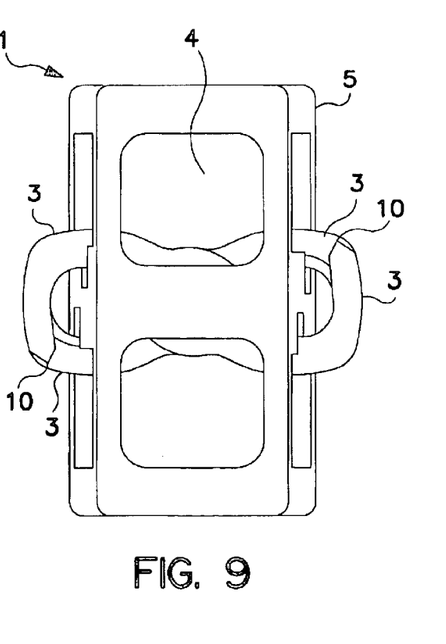

FIG. 9 illustrates the double S-shaped interbody cage, in the anchored position.

The cage is advantageously made from carbon or PEEK (poly ether ether ketone). Such materials have a Young's modulus comparable to that of bone and are also radiotransparent, leaving the practitioner a clearer vision of the bone progression during X-ray examinations. The anchoring means are advantageously made from hydroxyapatite or a bound and sintered calcium phosphate compound aggregate material. The aggregates are bound with calcium phosphate compound particles. The anchoring means may also be made from titanium or stainless steel-based metal alloy.

The anchoring means may also be made from bicalcium phosphate, tricalcium phosphate or porous tantalum.

Figure 10:
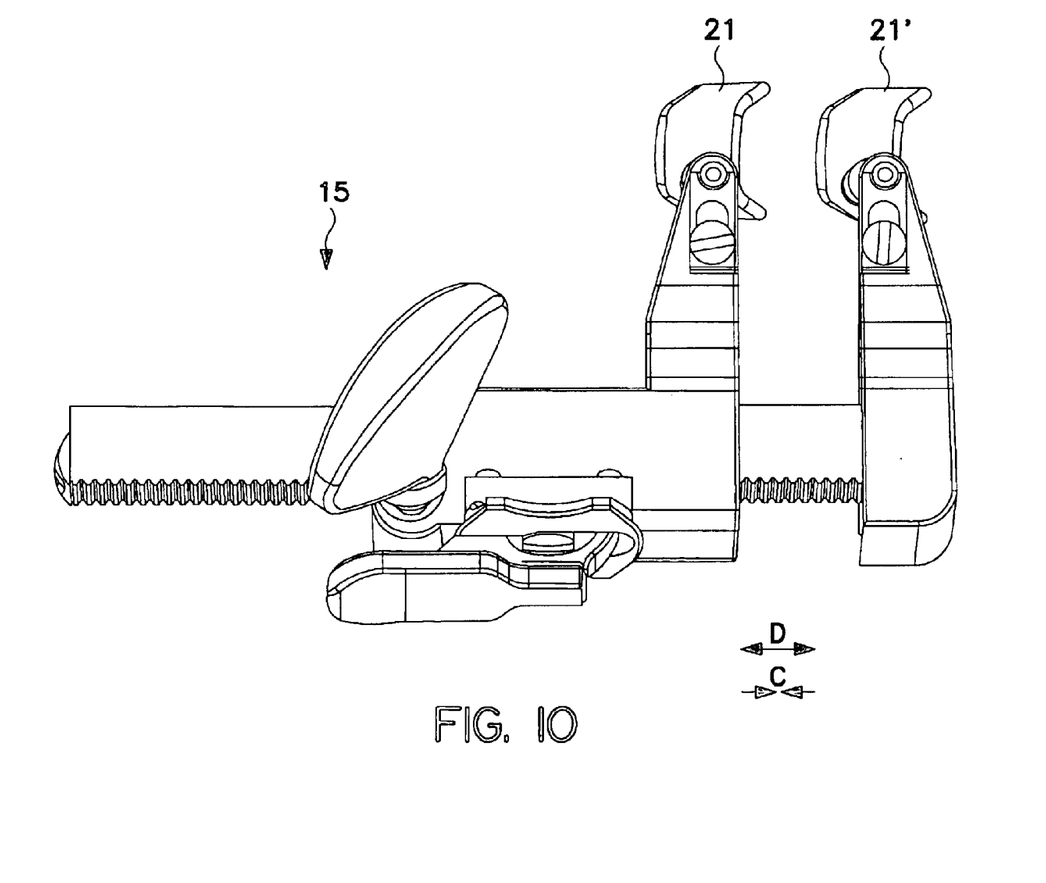
FIG. 10 illustrates the positioning of a compression/distraction instrument on the vertebrae.

To stabilize the spinal column, it is necessary to use a compression correction instrument C for the compression of the cage and sometimes a distraction instrument D for the preliminary work on the disk. Advantageously, a single instrument such as a compression/distraction instrument 15, as illustrated in FIG. 10, may be used. This instrument is fixed temporarily in the vertebral bodies of the vertebrae 21, 21'.

Figure 11:
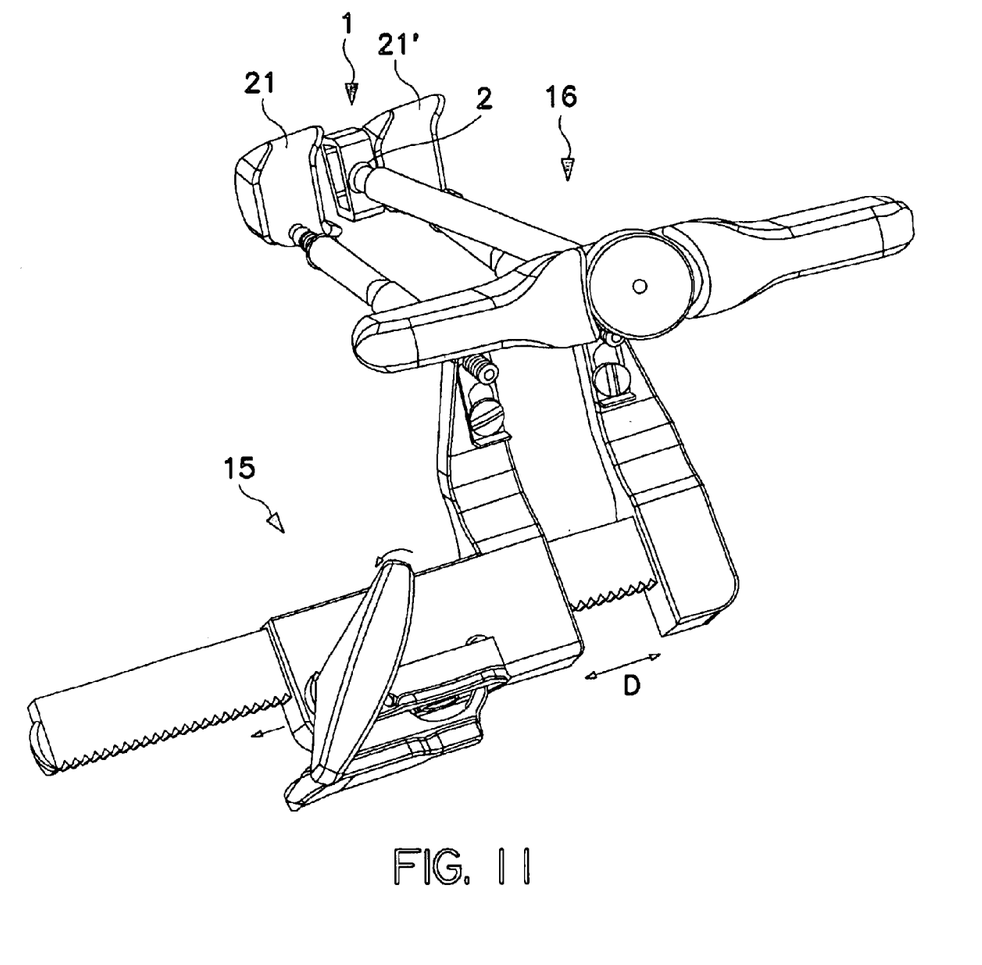
FIG. 11 illustrates distraction of the vertebrae prior to the anchoring of the interbody cage.

Prior to the anchoring of the cage, it is sometimes preferable to pre-cut the vertebral disks of the vertebrae between which the interbody cage is to be positioned, in order to facilitate the insertion of said anchoring means. For this, it is possible to use a separation instrument D of the vertebrae 21, 21', as illustrated in FIG. 11, followed by a cutting instrument of a shape adapted to that of the anchoring means.

The interbody cage 1 is inserted between the vertebrae 21, 21' using an anchoring means gripping and actuation instrument 16.

Figure 12:
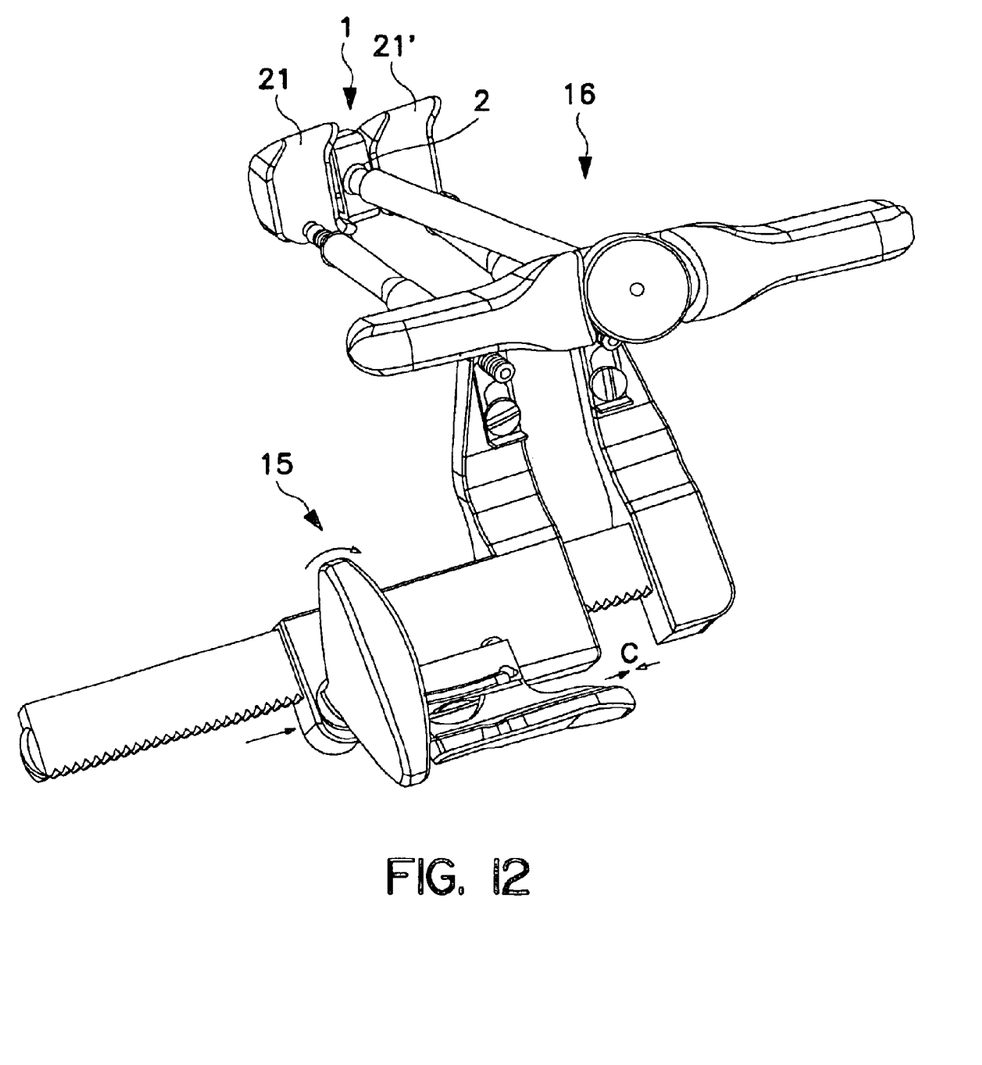
FIG. 12 illustrates compression of the vertebrae before the anchoring of the interbody cage.

During the anchoring of the cage, it is sometimes preferable to compress said vertebrae using a vertebral compression correction instrument C, as illustrated in FIG. 12.

Figure 13:
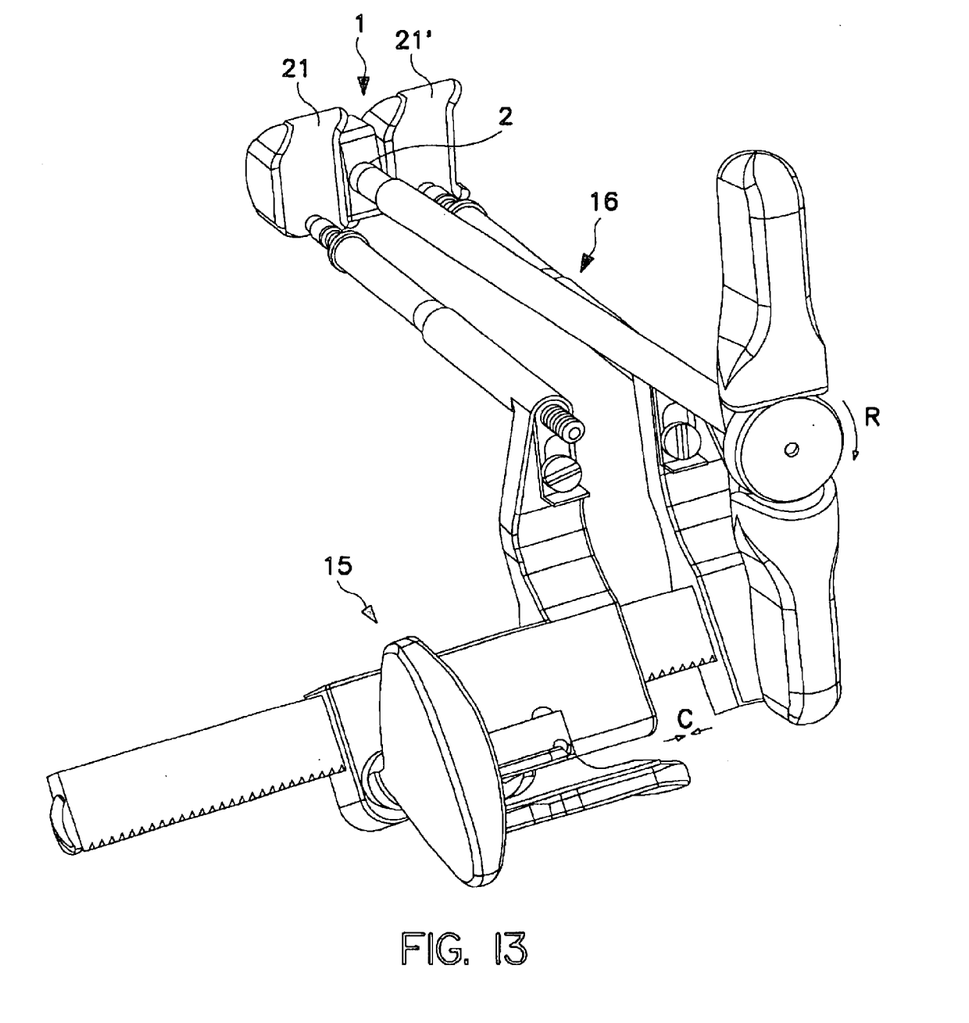
FIG. 13 illustrates the anchoring of the interbody cage in the vertebrae.

FIG. 13 illustrates the anchoring by means of rotation R of the actuation instrument 16 actuating the actuation means 2.

The invention is described above as an example. Those skilled in the art will be capable of producing various alternatives, particularly for the actuation of the anchoring means and the erection by means of actuation of an anchoring device accessible via a front face.

What is claimed is:

1. Interbody spinal stabilization cage having a parallelepipedic shape and comprising a central hollow space intended to be filled with bone fragments, said cage comprising anchoring means having an overall S shape and opening onto lateral faces connecting with adjacent vertebrae and being actuated by at least one actuation means opening into a front face, said anchoring means each comprising at least one main cutting edge.

2. Interbody cage according to claim 1, wherein the at least one actuation means comprises a rotation actuation head and is mobile in rotation in two directions, to allow reversibility of the anchoring means.

3. Interbody cage according to claim 1, wherein a center of gravity of the S shape is positioned on an axis of the at least one actuation means.

4. Interbody cage according to claim 1, wherein said at least one main cutting edge forms a base of at least an isosceles triangle equipped with cutting sides forming sharp edges.

5. Interbody cage according to claim 1, wherein each said anchoring means also comprises at least one radial cutting edge positioned on a radius of the anchoring means.

6. Interbody cage according to claim 1, wherein each said anchoring means also comprises at least one return cutting edge roughly parallel to the at least one main cutting edge.

7. Interbody cage according to claim 1, wherein each said anchoring means further comprises a slot.

8. Interbody cage according to claim 7, wherein edges of said slot are at least partially cutting.

9. Interbody cage according to claim 1, wherein said cage has force locking/unlocking means for maintaining the anchoring means in an anchored position.

10. Interbody cage according to claim 1, wherein said cage has two pairs of said anchoring means and each actuation means of each said pair of said anchoring means opens into the same front face.

11. Interbody cage according to claim 1, wherein each said actuation means has in its center a hole whose walls are threaded.

12. Spinal stabilization method using an interbody spinal stabilization cage positioned between two vertebrae and having a parallelepipedic shape and comprising a central hollow space intended to be filled with bone fragments, anchoring means having an overall S shape and opening onto lateral faces connecting with adjacent vertebrae, said S-shaped anchoring means being actuated by at least one actuation means opening into a front face and being used to actuate said S-shaped anchoring means in order to enable the S-shaped anchoring means to change from a retracted position wherein the S-shaped anchoring means are positioned inside said cage to a projecting position wherein ends of the S-shaped anchoring means come out of said cage, said anchoring means each comprising at least one main and cutting edge, said method comprising inserting said cage between two spinal vertebrae with the S-shaped anchoring means in the retracted position, and actuating the actuation means so that the ends of the S-shaped anchoring means come out of the cage and penetrate the vertebrae.

13. Spinal stabilization method using an interbody spinal stabilization cage according to claim 12, wherein vertebral disks of the vertebrae between which the interbody cage is to be positioned are cut beforehand.

14. Spinal stabilization method using an interbody spinal stabilization cage according to claim 12, wherein said vertebrae are compressed using a correction instrument during anchoring of said interbody cage.

15. A method for stabilizing a spine during a bone fusion procedure comprising:
providing an interbody stabilization cage having a parallelepipedic shape and comprising a central space for receiving bone fragments, anchoring means having an overall S shape and at least one main cutting edge, said anchoring means opening onto lateral faces connecting with adjacent vertebrae, and actuation means for operating said anchoring means;

implanting said cage to keep an intervertebral space between said adjacent vertebrae constant in order to prevent distraction of said vertebrae; and said implanting step comprising penetrating said anchoring means into the bone substance of at least one of said vertebrae.

16. A method according to claim 15, further comprising:

gathering bone fragments taken from a patient in said space; and using said bone fragments to initiate fusion of at least one of the vertebrae.

17. A method according to claim 15, wherein said implanting step further comprises locking said anchoring means in an anchoring position using a force locking/unlocking means.

18. A method according to claim 15, wherein said cage may be implanted using at least one of a cervical, thoracic and lumbar route.

19. A method according to claim 15, wherein said cage may be implanted using at least one of a frontal surgical procedure and a rear surgical procedure.

20. A method according to claim 15, further comprising removing said cage after said bone fusion procedure.

21. A method according to claim 15, wherein said anchoring means has at least one radial cutting edge and said penetrating step comprising moving said at least one radial cutting edge to cut into the bone structure of at least one vertebrae.

22. A method according to claim 15, wherein said anchoring means has at least one return cutting edge and said penetrating step comprising moving said at least one return cutting edge to cut into the bone structure of at least one vertebrae during an ablation movement.

23. A method according to claim 15, further comprising providing said actuation means with a center hole having threaded walls and using said center hole to position at least one additional component in an axis of the actuation means.

* * * * *